(12) United States Patent
Sicurella

(10) Patent No.: US 11,224,532 B2
(45) Date of Patent: Jan. 18, 2022

(54) ADJUSTABLE NECK REHABILITATION AND EXERCISE DEVICE AND METHOD FOR USE

(71) Applicant: Heidi Sicurella, Pacific Palisades, CA (US)

(72) Inventor: Heidi Sicurella, Pacific Palisades, CA (US)

( * ) Notice: Subject to any disclaimer, the term of this patent is extended or adjusted under 35 U.S.C. 154(b) by 516 days.

(21) Appl. No.: 16/168,592

(22) Filed: Oct. 23, 2018

(65) Prior Publication Data

US 2019/0117435 A1  Apr. 25, 2019

Related U.S. Application Data

(60) Provisional application No. 62/575,946, filed on Oct. 23, 2017.

(51) Int. Cl.
| | |
|---|---|
| *A61F 5/00* | (2006.01) |
| *A61F 5/055* | (2006.01) |
| *A61F 5/058* | (2006.01) |
| *A61F 5/042* | (2006.01) |

(52) U.S. Cl.
CPC .............. *A61F 5/055* (2013.01); *A61F 5/042* (2013.01); *A61F 5/05883* (2013.01)

(58) Field of Classification Search
None
See application file for complete search history.

(56) References Cited

U.S. PATENT DOCUMENTS

| | | | | | |
|---|---|---|---|---|---|
| 2,807,260 | A | * | 9/1957 | Teufel ..................... | A61F 5/055 602/17 |
| 3,365,926 | A | * | 1/1968 | Price ...................... | B21D 35/00 72/283 |
| 4,539,989 | A | * | 9/1985 | Forssmann .............. | A61B 6/12 601/4 |
| 4,827,915 | A | * | 5/1989 | Gorsen ................... | A61F 5/055 128/DIG. 23 |
| 4,955,368 | A | * | 9/1990 | Heimann ................ | A61F 5/055 128/DIG. 23 |
| 5,433,696 | A | * | 7/1995 | Osti ........................ | A61F 5/055 128/DIG. 23 |
| 5,624,387 | A | * | 4/1997 | McGuinness ........... | A61F 5/055 602/17 |

(Continued)

*Primary Examiner* — Kim M Lewis
(74) *Attorney, Agent, or Firm* — Perkins Coie LLP; Michael A. Glenn

(57) ABSTRACT

A neck rehabilitation apparatus is disclosed. The neck rehabilitation apparatus may include a ring-shaped neck piece including a plurality of slots formed through the neck piece, and a ring-shaped chest piece including a plurality of slots formed through the chest piece. The apparatus may include at least four adjustable support members. Each adjustable support member may include a first end configured to engage with at least one slot formed through the neck piece, a second end configured to engage with at least one slot formed through the chest piece, a telescoping member configured to be adjustably moved to a selected position, and a telescoping member locking mechanism configured to lock the telescoping member at the selected position. The neck rehabilitation apparatus may provide varying degrees of support during rehabilitation of head and/or neck muscles and vertebrae.

17 Claims, 13 Drawing Sheets

(56) References Cited

U.S. PATENT DOCUMENTS

| | | | |
|---|---|---|---|
| 2008/0004556 A1* | 1/2008 | Gehlbach | A61F 5/055 602/18 |
| 2009/0149788 A1* | 6/2009 | Dellanno | A61F 5/055 602/18 |
| 2009/0187129 A1* | 7/2009 | Ben-Galim | A61F 5/055 602/18 |
| 2010/0087764 A1* | 4/2010 | Linares | A61F 5/055 602/18 |
| 2010/0211105 A1* | 8/2010 | Moumene | A61B 17/7025 606/258 |
| 2015/0190266 A1* | 7/2015 | Hollern | A61F 5/055 602/18 |
| 2016/0220410 A1* | 8/2016 | Hwang | A61F 5/055 |

* cited by examiner

ADJUSTABLE NECK REHABILITATION AND EXERCISE DEVICE AND METHOD FOR USE

CROSS-REFERENCES TO RELATED APPLICATIONS

This application claims the benefit of and/or the right of priority to U.S. Provisional Patent Application No. 62/575,946 entitled "ADJUSTABLE NECK REHABILITATION AND EXERCISE DEVICE AND METHOD FOR USE," which was filed on Oct. 23, 2017; the contents of which are incorporated by reference in their entirety within.

BACKGROUND

In the event of an injury to muscles or vertebrae in a user's neck area, a support device may be utilized to assist in healing the injured area. Common support devices may include a neck brace or neck collar, for example. Support devices may partially or fully immobilize the muscles and vertebrae of the injured area to allow the injured area to heal without agitation by an external force (e.g., the weight of a human head, or tension from turning the neck). A support device generally provides a threshold amount of support to the neck and head of a user, thereby relieving at least some pressure from the injured area. Muscles and vertebrae in the neck may heal over an extended period of time, and it generally takes an extended period for injured muscles to heal and regain strength. A support device may relieve pressure from the injured area and provide greater comfort to the user while the injured muscles and vertebrae heal.

SUMMARY

Some of the subject matter described herein includes a neck rehabilitation apparatus comprising: a ring-shaped neck piece including a plurality of slots formed within the neck piece; a ring-shaped chest piece including a plurality of slots formed within the neck piece; and at least four adjustable support members, each of the at least four adjustable support members comprising: a static member, a telescoping member adjustably movable along the static member to a selected position, where the selected position of the telescoping member determines a fixed, spaced relation between the neck piece and the chest piece, the telescoping member comprising: a first end engageable with at least one slot formed in the neck piece; and a second end engageable with at least one slot formed in the chest piece; and a telescoping member locking mechanism configured to lock the telescoping member at the selected position.

In some implementations, each of the at least four adjustable support members include a concave curvature that follows the curvature of a human neck.

In some implementations, the neck rehabilitation apparatus further includes two front adjustable support members and two rear adjustable support members, where the two rear adjustable support members have a greater length than the two front adjustable support members.

In some implementations, the first end and the second end of each adjustable support member includes a slot engaging member, wherein the slot engaging member at the first end is configured to engage at least one slot of the neck piece, and the slot engaging member of the second end is configured to engage at least one slot of the chest piece.

In some implementations, the telescoping member includes a plurality of openings formed therein.

In some implementations, the telescoping member locking mechanism extends outwardly from a static member of each adjustable support member, where the telescoping member locking mechanism is configured to frictionally engage with one of the plurality of openings of the telescoping member.

Some of the subject matter described herein includes an apparatus comprising: a ring-shaped neck piece including a plurality of slots formed within the neck piece; a ring-shaped chest piece including a plurality of slots formed within the chest piece; and at least four adjustable support members, each of the at least four adjustable support members including: a static member; a telescoping member adjustably movable along the static member to a selected position, where the selected position of the telescoping member determines a fixed, spaced relation between the neck piece and the chest piece, the telescoping member comprising: a first end including a slot engaging member engaged with at least one slot formed in the neck piece; and a second end including a second slot engaging member engaged with at least one slot formed in the chest piece; and a telescoping member locking mechanism locking the telescoping member at the selected position.

In some implementations, a neck wrap is configured to frictionally engage to the neck piece and the chest piece.

In some implementations, the neck wrap frictionally engages to the neck piece and chest piece using a plurality of buttons disposed along the neck piece and chest piece.

In some implementations, the neck wrap, neck piece, and chest piece form a single piece which wraps around the neck and is frictionally engaged at the faces of the neck and chest pieces.

In some implementations, the neck wrap, neck piece, and chest piece form a single piece which wraps around the neck and is frictionally engaged using a plurality of buttons disposed along the neck wrap portion of the single piece.

In some implementations, a bladder is formed within the neck wrap.

In some implementations, a liquid is disposed within the bladder

In some implementations, a chin plate is engaged to the neck piece, where the chin plate is configured to be disposed below a chin of a user.

In some implementations, an over-the-shoulder stabilizer is engaged to the chest piece, where the over-the-shoulder stabilizer is engaged to and extends downward from the chest piece.

Some of the subject matter described herein includes a method comprising: engaging a first end of each of least four adjustable support members into a slot formed within a ring-shaped neck piece; engaging a second end of each of the at least four adjustable support members into a slot formed within a ring-shaped chest piece; adjustably moving a telescoping member disposed along each of the at least four adjustable support members to a selected position; and locking the telescoping member at the selected position by a telescoping member locking mechanism.

In some implementations, engaging the first end of each of least four adjustable support members includes engaging a slot engaging member with the slot formed within the neck piece.

In some implementations, engaging the second end of each of least four adjustable support members includes engaging a second slot engaging member with the slot formed within the chest piece.

In some implementations, locking the telescoping member includes engaging the telescoping member locking mechanism with one of a plurality of openings formed within the telescoping member, wherein the telescoping member locking mechanism extends outwardly from the adjustable support member.

In some implementations, the method includes unlocking the telescoping member locking mechanism from the telescoping member; moving the telescoping member to a second selected position; and locking the telescoping member locking mechanism at the second selected position.

DETAILED DESCRIPTION

Injury to neck muscles and/or vertebrae may result from a variety of causes. In the event of such an injury, the injured area may be unable to provide support to the head and neck of the user. Neck support devices may be used to provide support to the injured area. Neck support devices may partially or fully immobilize the neck to prevent sudden movement of the neck that may cause further injury or discomfort to the user.

The healing time of the injured neck muscles or vertebrae may be extensive. During the healing time and immobilization by a neck support device, the injured area and the portions of the neck and shoulder muscles otherwise uninjured may weaken and atrophy. When the neck support device is removed, the collective strength of the neck muscles may be insufficient to support the weight of the head in a position of proper posture. In some instances, the neck may begin to descend into the shoulders as the disks between vertebrae condense or herniate under the additional weight. The time to rehabilitate the appropriate muscles to regain strength may be extensive. As a result, a person may experience substantial discomfort and pain during the healing and rehabilitation time, and may be unable to engage in common activities like exercise.

A neck rehabilitation apparatus includes a ring-shaped neck piece including a plurality of slots formed within the neck piece. A ring-shaped chest piece includes a plurality of slots formed within the chest piece. At least four adjustable support members include a first end configured to engage with at least one slot formed in the neck piece and a second end configured to engage with at least one slot formed in the chest piece. A telescoping member of the adjustable support member is configured to be adjusted to a selected position, and a telescoping member locking mechanism is configured to lock the telescoping member at the selected position.

Figure 1:
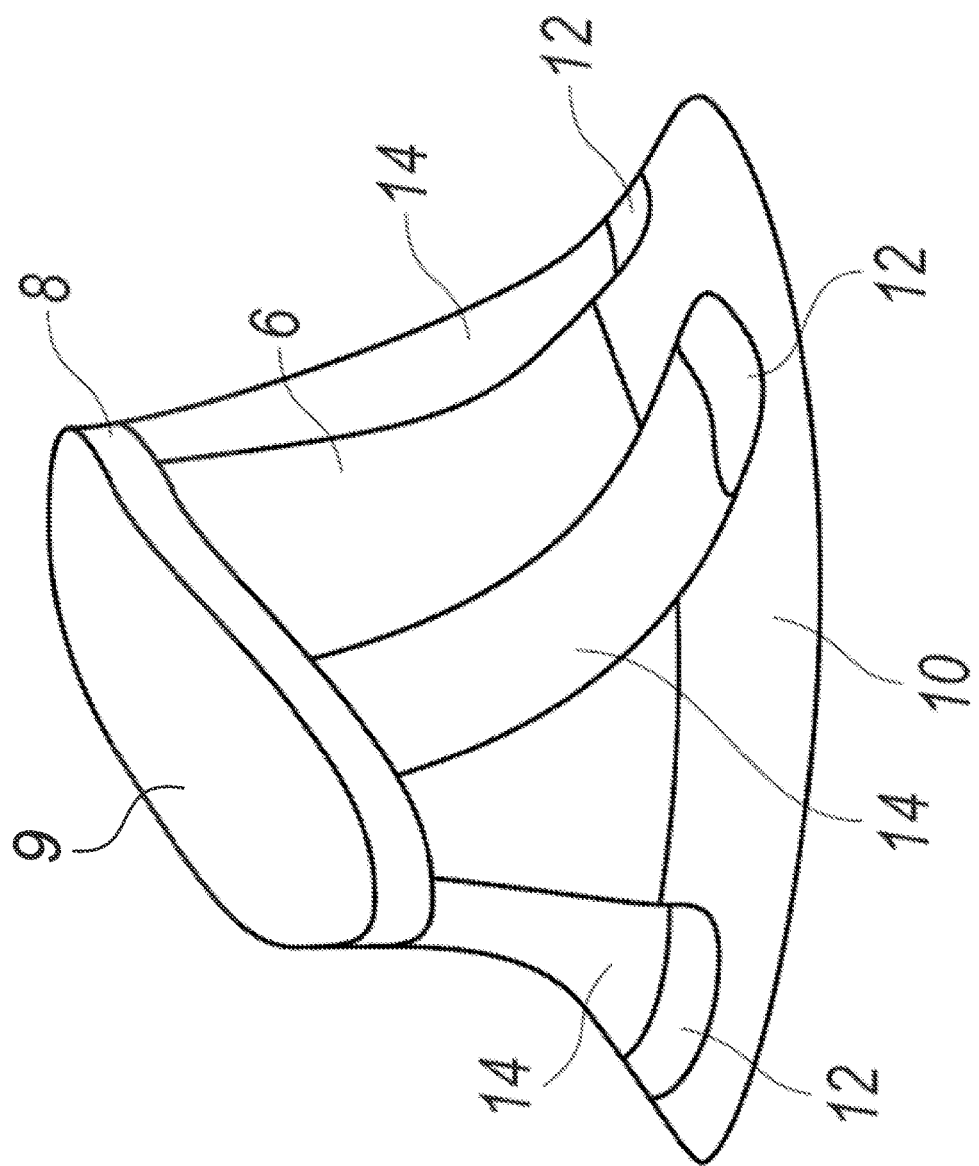
FIG. 1 illustrates a front view of neck rehabilitation apparatus, consistent with various embodiments.

FIG. 1 illustrates a front view of neck rehabilitation apparatus 100, consistent with various embodiments. The apparatus 100 includes a neck piece 8, a chest piece 10, and at least four adjustable support members 14.

The apparatus 100 includes a ring-shaped neck piece 8. The ring-shaped neck piece 8 may be referred to as a neck piece 8. The neck piece 8 may be substantially ring shaped. The neck piece 8 may include an opening 9 formed within the neck piece 8, where the opening 9 may be configured to receive the head of a user. The neck piece 8 may be contoured to follow the general shape of the lower portion of a human head.

The neck piece 8 may include a plurality of slots 12. Each of the plurality of slots 12 may be formed within the neck piece 8. Each slot 12 may be configured to receive an end of an adjustable support member 14. Each slot 12 may be substantially elliptical, rectangular, circular, or another suitable shape. The neck piece 8 may include any suitable number of slots 8, such as four slots, for example.

In some embodiments, the neck piece 8 comprises a thick fabric material. The thickness of the fabric material may include any suitable thickness to provide sufficient support to the neck and head of a user. Any suitable material that increases stability of the neck piece 8 and withstands the forces provided by a human head, for example, may be included. The neck piece 8 material may include a suitable indicia of flexibility to accommodate the varying head and neck dimensions of different human users. In some embodiments, the neck piece 8 may include a dense foam material.

The apparatus 100 includes a ring-shaped chest piece 10. The ring-shaped chest piece 10 may be referred to as a chest piece 10. The chest piece 10 may be substantially ring shaped. The chest piece 10 may include an opening 9 formed within the chest piece 10. The opening 9 of the chest piece 10 may comprise a greater area than the opening 9 of the neck piece 8. The chest piece 10 may be contoured to resemble the general shape of the upper chest and shoulders of a human user. The chest piece 10 may include a plurality of slots 12. The plurality of slots 12 may be substantially similar to the plurality of slots 12 in the neck piece 8. The neck piece 8 and/or the chest piece 10 may be configured to be adjustable in size.

The chest piece 10 may be composed of a thick fabric material, where the thickness is any suitable thickness of fabric to support the apparatus 100. In some embodiments, the neck piece 8 and the chest piece 10 comprise the same material. However, because the contours of the shoulder and chest area differ from the contours of the neck and head area, the size of the neck piece 8 may be smaller than the chest piece 10. The chest piece 10 may include a more malleable and flexible material than the neck piece 8 so that a single apparatus 100 accommodates a variety of users. Further, because the shoulder and chest areas are not as sensitive as the neck and face, the chest piece 10 may include a tougher and/or more rigid material.

The apparatus 100 includes at least four adjustable support members 14. The apparatus 100 may include any suitable number of adjustable support members, but four adjustable support members 14 may be illustrated in some embodiments. Each adjustable support member 14 may be configured to engage with at least one slot formed in the neck piece 8 and at least one slot formed in the chest piece 10.

The adjustable support members 14 may be comprised of two or more pieces of dense fabric material. Dense fabric may be utilized instead of a rigid material, e.g. metal, because the ordinary user's neck is very sensitive as the user overcomes an injury to the neck area. In some embodiments, the components, such as the adjustable support members 14, for example, may include a fabric material disposed along the periphery of a metal material. A fabric of the adjustable support members 14 may be sufficiently rigid to exert pressure along its adjustable axis to help extend the user's spine. In some embodiments, the fabric is comparable to a backpack strap or an over-the-counter wrist brace in terms of rigidity. However, any material with non-negligible flexibility along the adjustable axis may be utilized, and the appropriate flexibility may vary across the spectrum of users and may be tailored to an individual user's or classes of users (e.g., smaller children, animals) and particular sensitivities (e.g., atrophied muscles and other physical limitations).

Figure 2:
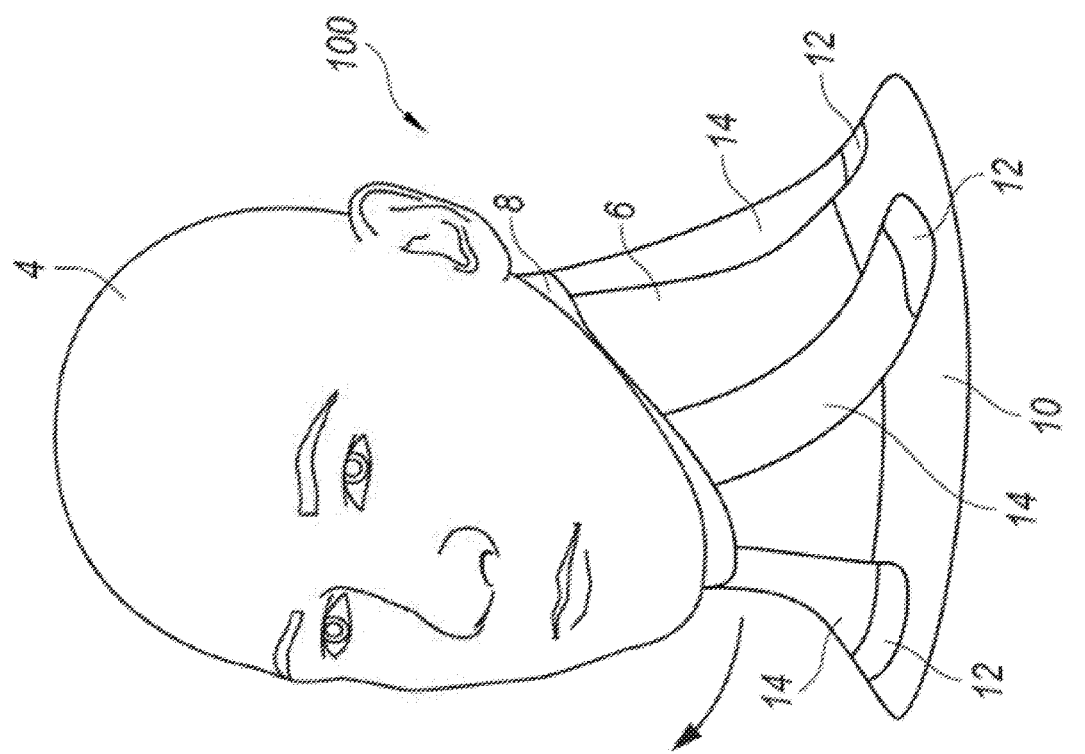
FIG. 2 illustrates a front view of a neck rehabilitation apparatus in use, consistent with various embodiments.

FIG. 2 illustrates a front view of a neck rehabilitation apparatus 100 in use, consistent with various embodiments. The apparatus 100 may provide support to rehabilitate injured muscles or vertebrae of a user 4. As shown in FIG. 2, the apparatus 100 may be in contact with the head, neck, shoulders, and/or chest of a user 4.

As illustrated in FIG. 2, the neck piece 8 may be in contact with the lower head portion of the user and/or the upper neck of the user 4. The chest piece 10 may contact the upper chest and/or shoulders of the user 4. The adjustable support members 14 may be disposed between the neck piece 8 and chest piece 10. The adjustable support members 14 may contact the neck of the user 4 and may be disposed in parallel with the spinal structure of the user 4. With the neck rehabilitation apparatus 100, user 4 may have limited rotational capability, but no capability to move their head in a downward direction, as the adjustable support members 14 supports the head from below. As shown in FIG. 2, the apparatus 100 may include a neck wrap 6. The neck wrap 6 may be disposed between the neck piece 8 and chest piece 10. The neck wrap 6 may be disposed around the entire periphery of both the neck piece 8 and the chest piece 10. When engaged to a user, the neck wrap 6 may at least reach or cover the C-7 vertebrae. The neck wrap 6 may be frictionally attached to the neck piece 8 and chest piece 10, or instead may comprise a single piece that includes the neck piece 8 and chest piece 10.

Figure 3:
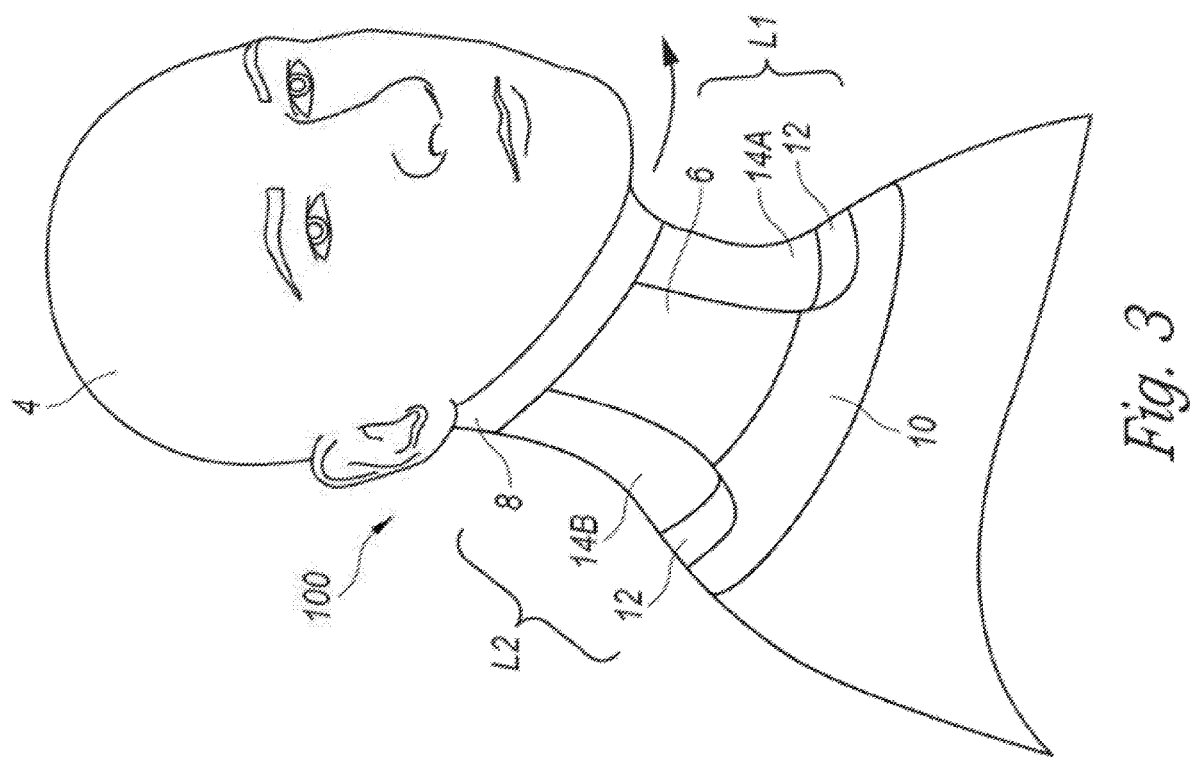
FIG. 3 illustrates a side view of a neck rehabilitation apparatus in use, consistent with various embodiments.

FIG. 3 illustrates a side view of a neck rehabilitation apparatus 100 in use, consistent with various embodiments. As shown in FIG. 3, adjustable support members 14 are disposed between the neck piece 8 and the chest piece 10. In some embodiments, four total adjustable support members 14 are included, including two front adjustable support members 14A and two rear adjustable support members 14B. The front adjustable support members 14A may include a length L1, and the rear adjustable support members 14B may include a length L2.

As shown in FIG. 3, the rear adjustable support members 14B length L2 may be greater than the front adjustable support members 14A length L1. Due to the curvature of the human neck, the rear portion of the neck may include a greater length than the front portion of the neck.

Figure 4:
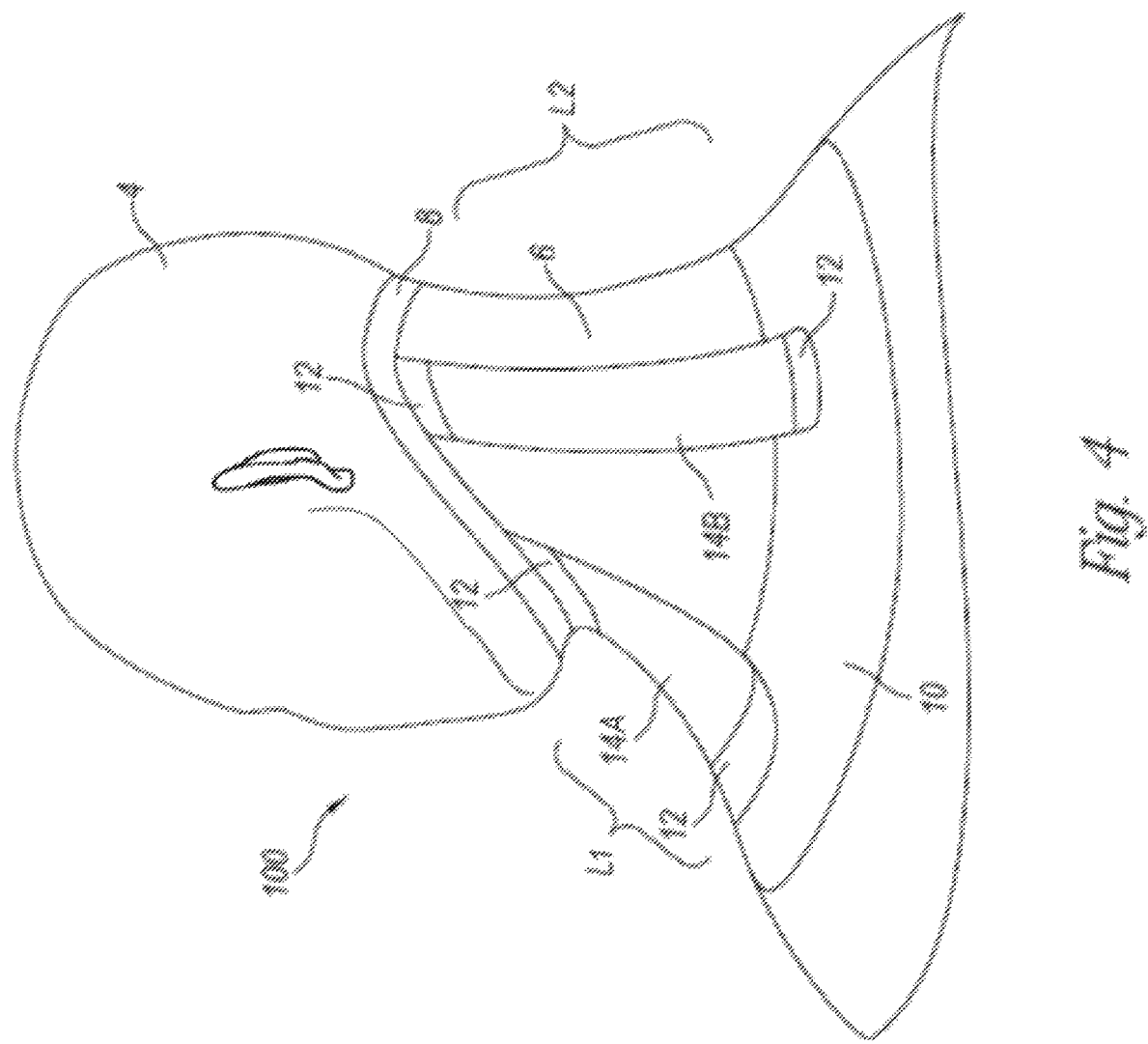
FIG. 4 illustrates a back view of a neck rehabilitation apparatus in use, consistent with various embodiments.

FIG. 4 illustrates a back view of a neck rehabilitation apparatus 100 in use, consistent with various embodiments. The apparatus 100 illustrates two rear adjustable support members 14B, each including length L2. Each rear adjustable support member 14B may include a substantially similar length L2. The adjustable support members 14 may include a curvature that follows the curvature of the neck.

Figure 5:
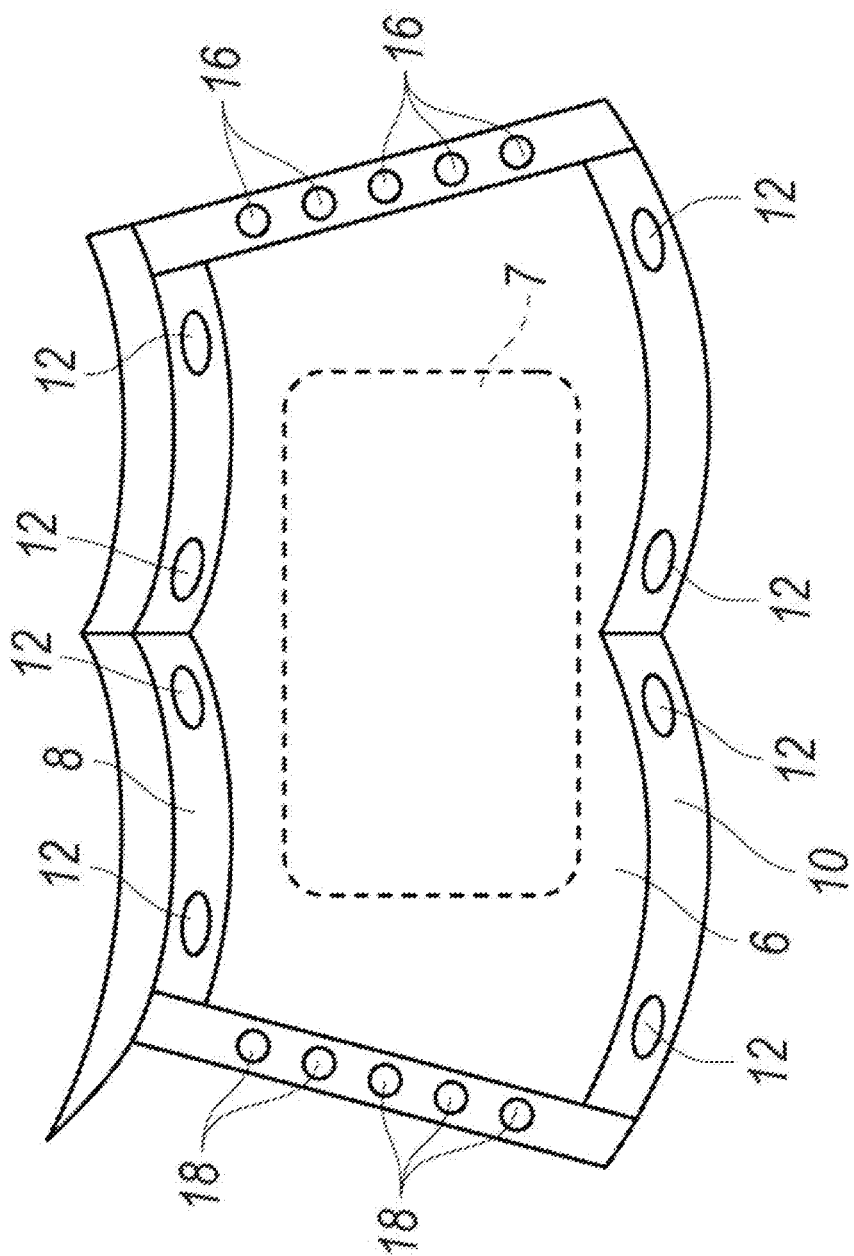
FIG. 5 illustrates an exploded view of a neck rehabilitation apparatus, consistent with various embodiments.

FIG. 5 illustrates an exploded view of a neck rehabilitation apparatus 100, consistent with various embodiments. As shown in FIG. 5, the neck wrap 6 may be engaged to both the neck piece 8 and the chest piece 10. The neck wrap 6 may engage to the neck piece 8 and chest piece 10 using a connector such as buttons, hook and loop, snap buttons, straps, for example. In some embodiments, the neck wrap 6, neck piece 8, and chest piece 10 may be attached in a manner that would not permit easy detachment (i.e., may be sewn, fused, or otherwise adhered together). In some embodiments, the neck wrap 6 includes snap buttons 16 that are configured to engage with snap button holes 18. The neck wrap 6 may be removably attached to the neck piece 8 and chest piece 10.

A bladder 7 may be formed within the neck wrap 6. The bladder 7 may be configured to be filled with a suitable liquid or gas. The liquid may be cool or warm in temperature to provide heat or cooling to the neck of the user.

Because some users do not ordinarily cover their neck area, the user may experience discomfort from the fabric covering the neck area, especially due to overheating. To resolve this, a user may fill the bladder 7 with a gas or liquid in a cooled environment (e.g., in a refrigerator or freezer) before use. Some types of bladder 7 filling (e.g., water) effectively retain heat, so a user may place fabric material in a warm environment if the user desires that the neck area be warmed. In some embodiments, the fabric is capable of retaining its initial temperature. Embodiments of the apparatus 100 for small children may include colorful designs to create aesthetic appeal that encourages consistent use.

The neck wrap 6 may be composed of fabric material. Because the material is applied directly to human skin and remains in application for some time, the neck wrap 6 material may be soft, and either breathable or wicking (for example, material used in athletic wear). The material may include an indicia of flexibility in all directions to provide a single neck wrap piece 6 that may be worn by a number of human users, each having a different neck circumference and/or length. Some embodiments may include a variety of different sized fabrics to provide more tailored fits toward certain classes of users (for example, small children).

Figure 6:
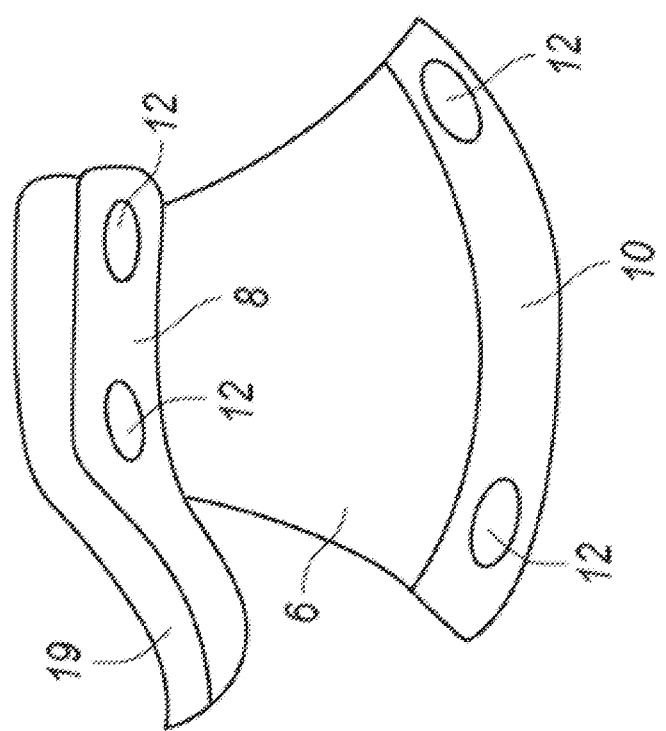
FIG. 6 illustrates a side view of a neck rehabilitation apparatus, consistent with various embodiments.

FIG. 6 illustrates a side view of a neck rehabilitation apparatus 100, consistent with various embodiments. As shown in FIG. 6, the apparatus may include a chin plate 19. The chin plate 19 may be engaged to the neck piece 8. In some embodiments, the neck piece 8 may include a single component that includes a chin plate 19 expanding outwardly from the neck piece 8. The chin plate 19 may be configured to support a chin of the user.

Figure 7:
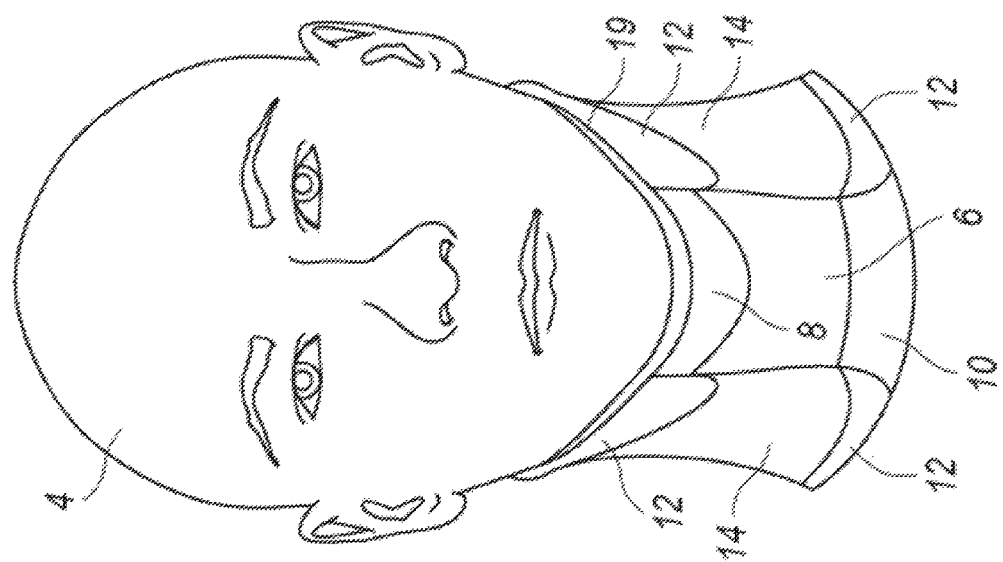
FIG. 7 illustrates a view of a neck rehabilitation apparatus, from the perspective of below the human user, consistent with various embodiments.

FIG. 7 illustrates a view of a neck rehabilitation apparatus 100, from the perspective of below the human user, consistent with various embodiments. The chin plate 19 may be disposed around a front half of the neck piece 8. The chin plate 19 may support the chin of the user 4. The chin plate 19 may prevent movement of the head and/or chin of the user by immobilizing the chin of the user 4.

The chin plate 19 may include a thick piece of fabric that may rest along the underside of the chin. In an embodiment, the orientation of the chin plate 19 relative to a human user is as shown in FIG. 7. Note that the view presented is from below the human user, and not as if the human user were looking upward. In practice, a user wearing the apparatus 100 may be unable to look upward while wearing the apparatus 100 or while rehabilitating their injury.

Figure 8:
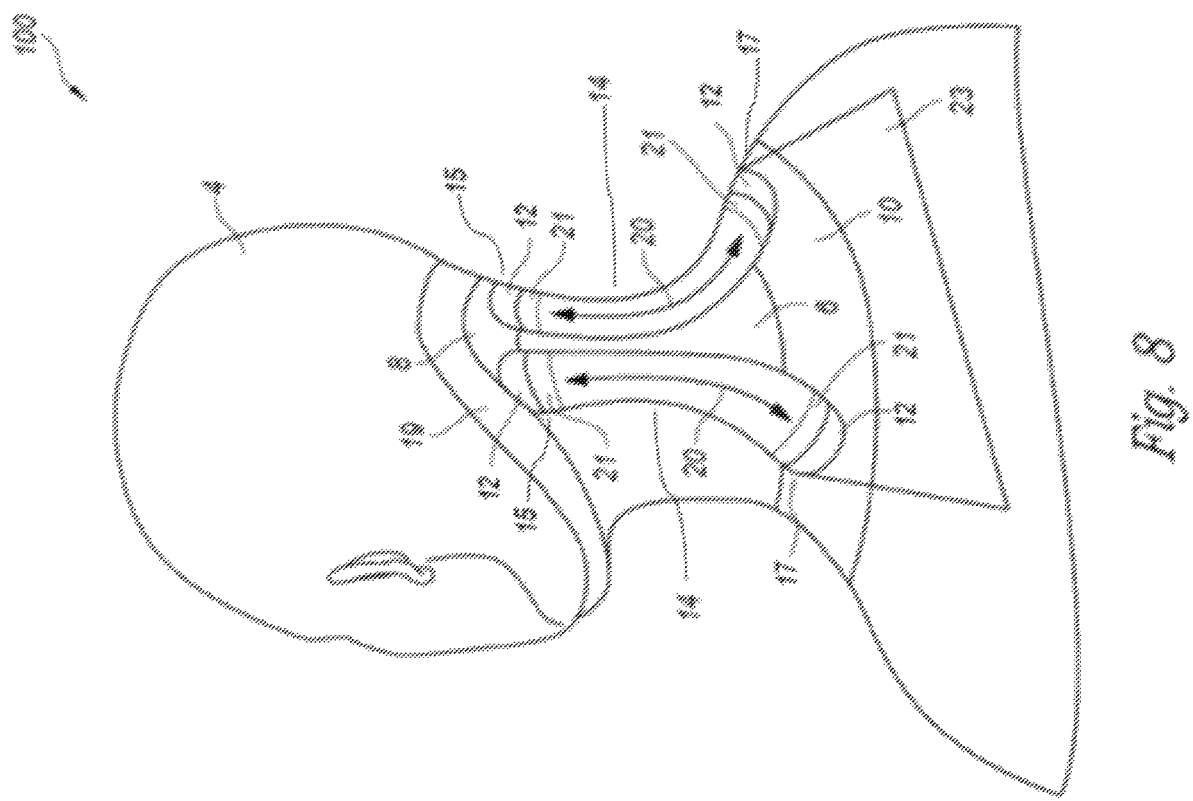
FIG. 8 illustrates a back view of a neck rehabilitation apparatus, consistent with various embodiments.

FIG. 8 illustrates a back view of a neck rehabilitation apparatus 100, consistent with various embodiments. As shown in FIG. 8, the adjustable support members 14 may be adjusted along axis 20. In some embodiments, each adjustable support member 14 includes a first end 15 and a second end 17. The first end 15 may be disposed at the periphery of each adjustable support member 14. The first end 15 may be configured to connect to a slot 12 of the neck piece 8. The second end 17 may be configured to connect to a slot 12 of the chest piece 10. The first end 15 and the second end 17 of each adjustable support member 14 may be disposed at opposing ends.

A slot engaging member 21 may be disposed at each of the first end 15 and the second end 17 of each adjustable support member 14. Each slot engaging member 21 may be configured to engage with one or more slots 12 of either the neck piece 8 or the chest piece 10. As shown in FIG. 8, slot engaging member 21 may be disposed at a first end 15 of an adjustable support member 14 and engaged to a slot 12 of the neck piece 8. Similarly, a slot engaging member 21 at the second end 17 of an adjustable support member 14 may be engaged to a slot 12 of chest piece 10. In some embodiments, each slot engaging member 21 disposed on an adjustable support member 14 may engage the adjustable support member 14 to the neck piece 8 and chest piece 10.

The slot engaging member 21 may include a protrusion that frictionally engages with a slot 12. The slot engaging member 21 may rotationally engage with the slot. The slot engaging member 21 may include a suitable connection mechanism sufficient to withstand the forces associated with using the neck rehabilitation apparatus 100 including, for example, a hook-loop or slide-to-lock mechanism.

The apparatus 100 may include an over-the-shoulder stabilizer 23. The over-the-shoulder stabilizer 23 may be configured to provide stability to the back and/or shoulders of the user. The over-the-shoulder stabilizer 23 may be engaged with the chest piece 10. The chest piece 10 may comprise a single piece that includes the over-the-shoulder stabilizer 23 protruding downward from the chest piece 10. The over-the-shoulder stabilizer 23 may provide additional stability because the forces exerted by the bottom piece are distributed over a broader area. The over-the-shoulder stabilizer 23 may comprise a material that provides both comfort and stability, as it is designed to reduce the stress applied in order to improve the rehabilitation process. In some embodiments, the over-the-shoulder stabilizer 23 includes the rigidity of a material comparable to a backpack strap or an over-the-counter wrist brace. It also is contemplated that the over-the-shoulder stabilizer 23 includes any material with a suitable rigidity.

Figure 9:
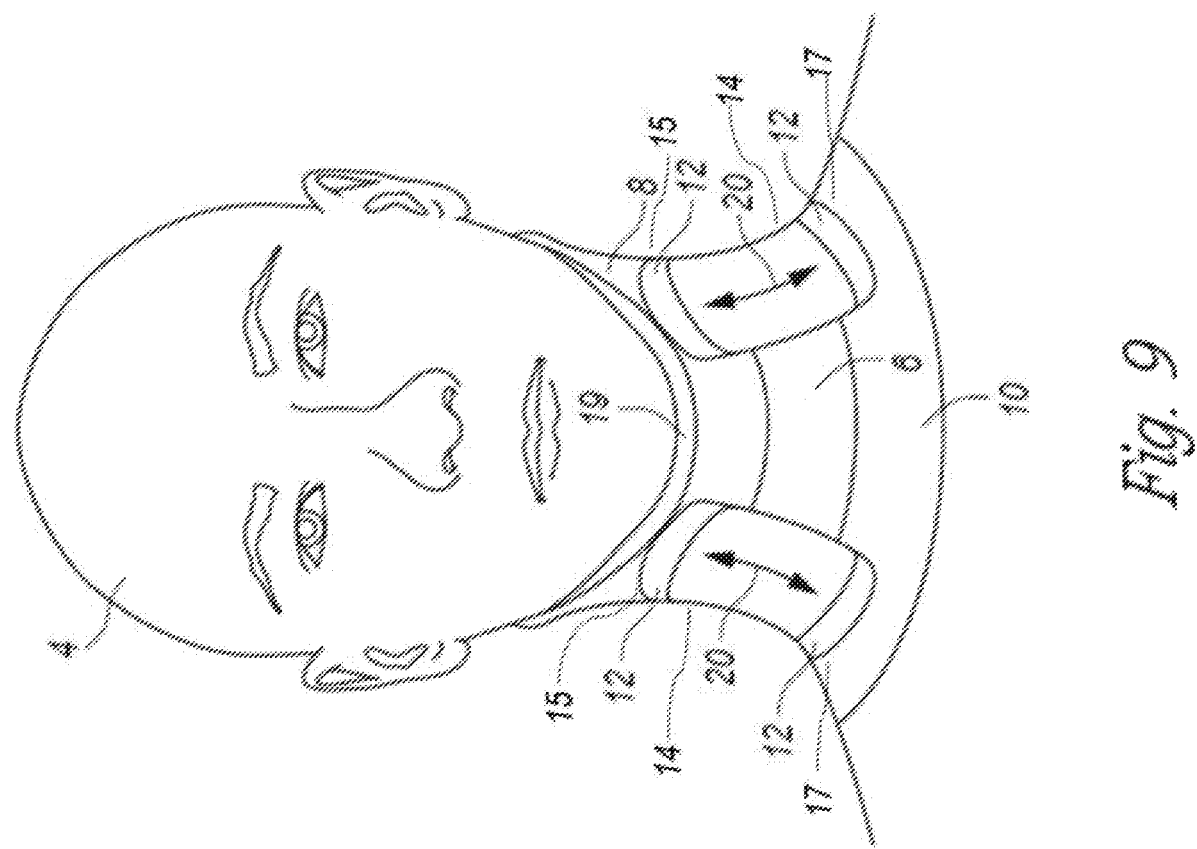
FIG. 9 illustrates a front view of a neck rehabilitation apparatus, consistent with various embodiments.

FIG. 9 illustrates a front view of a neck rehabilitation apparatus, consistent with various embodiments. As shown in FIG. 9, the adjustable support members 14 provide support to the head and neck of a user 4. The adjustable support members 20 may provide support in the direction shown by the arrows 20.

The adjustable support members 14 may comprise a dense fabric material containing a series of openings configured to lock each extender in a selected position. For example, some embodiments of the adjustable support members 14 include a suitable plastic material.

Figure 10:
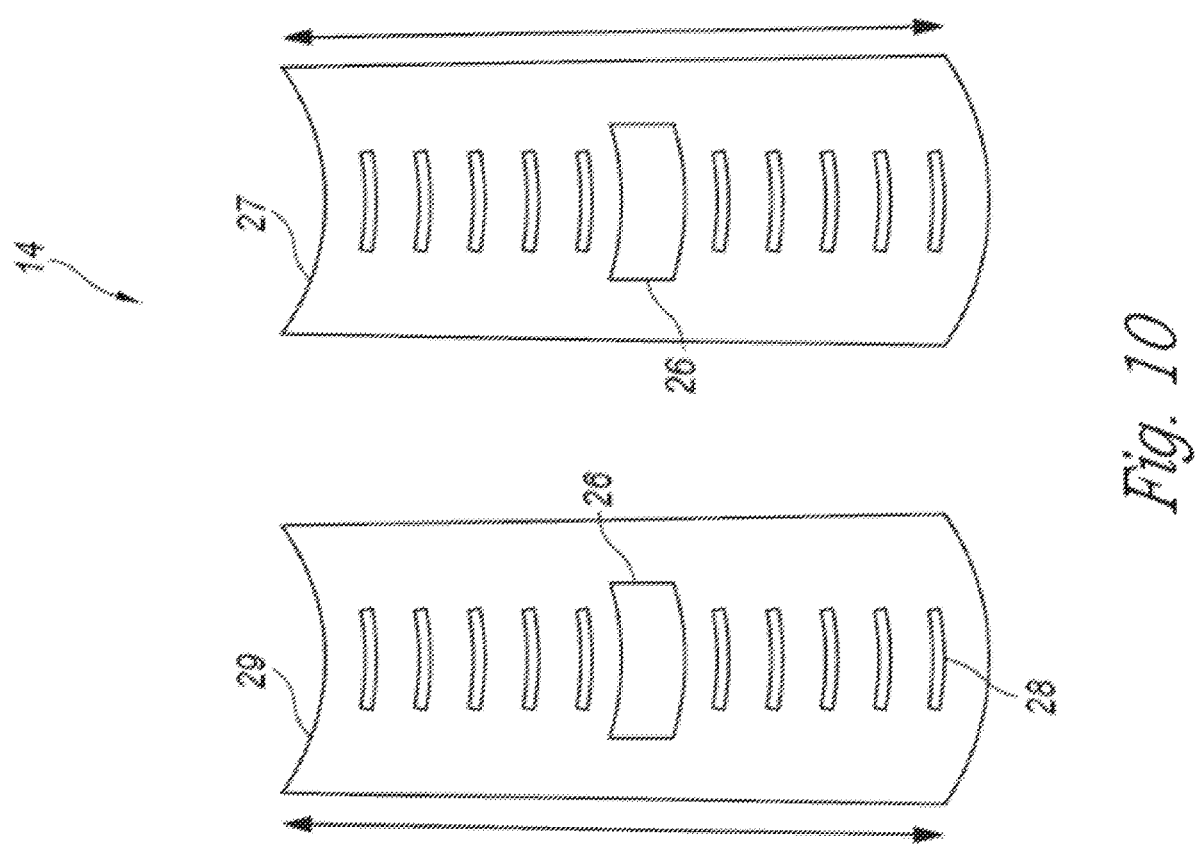
FIG. 10 illustrates a front view of an adjustable support member, consistent with various embodiments.

FIG. 10 illustrates a front view of an adjustable support member 14, consistent with various embodiments. The adjustable support member 14 may include a static member 27 and a telescoping member 29. The static member 27 and telescoping member 29 may be disposed in parallel with one another and in contact with one another. The static member 27 may be configured to remain static and not move. The telescoping member 29 may be configured to adjustably move along the static member 27. The telescoping member 29 may expand the overall length of the adjustable support member 14 by adjustably moving along the static member 27. The telescoping member 29 may move in the direction as shown by the arrows.

The telescoping member 29 may be movably adjusted along the static member 27 to adjust the total length of the adjustable support member 14. The adjustable support member 14 may include a telescoping member locking mechanism 26. The telescoping member locking mechanism 26 may be disposed on at least one of the static member 27 and the telescoping member 29. In some embodiments, the telescoping member locking mechanism 26 may be disposed on the static piece 27.

The telescoping member locking mechanism 26 may include a protrusion that is configured to extend into an opening 28 disposed along the telescoping member 29. The telescoping member locking mechanism 26 may include any suitable locking mechanism to frictionally engage with an opening 28, such as a button, snap button, or an extension extending outward from the static piece, for example.

The telescoping member locking mechanism 26 may be configured to lock the telescoping member 29 at a selected position. The selected position may include the location of the telescoping member 29 that is adjustably moved along the static member 27. The selected position may be determined by the user to provide a proper amount of support to the head and neck of the user. The telescoping member 29 may include a plurality of openings 28 disposed along the telescoping member 29. Each opening 28 may represent a different position of the telescoping member 29 when locked in place. Adjusting the adjustable support members 14 via locking the telescoping member 29 may allow for the user to rehabilitate muscles and vertebrae of the user.

Figure 11:
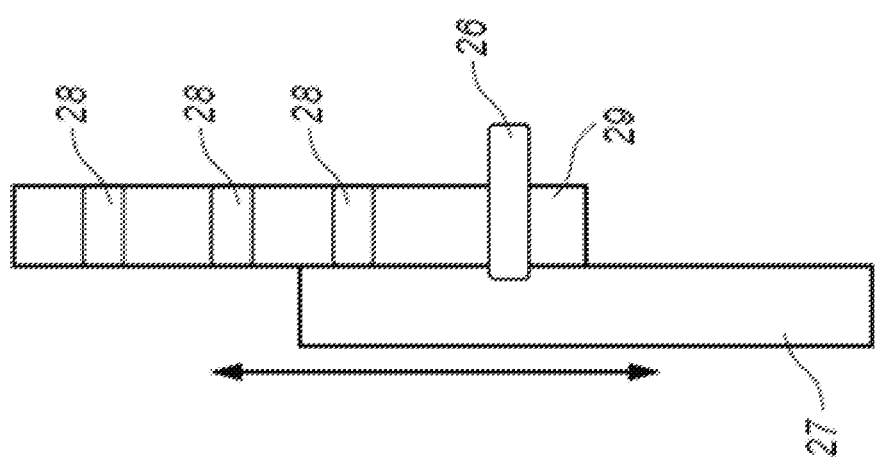
FIG. 11 illustrates a side view of an adjustable support member, consistent with various embodiments.

FIG. 11 illustrates a side view of an adjustable support member 14, consistent with various embodiments. As shown in FIG. 11, the telescoping member 29 may adjustably move along the axis shown by the arrows. The telescoping member locking mechanism 26 may lock the telescoping member at the selected position by extending the telescoping member locking mechanism 26 through an opening 28 formed within the telescoping member 29. The telescoping member locking mechanism 26 may frictionally engage to the telescoping member 29 via an opening 28.

Figure 12:
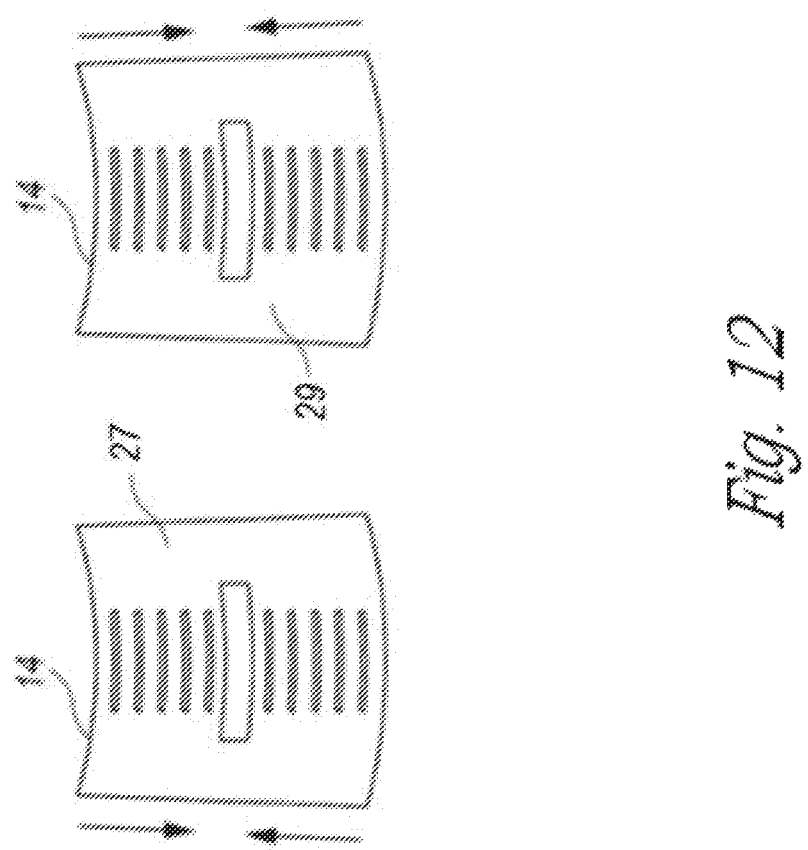
FIG. 12 illustrates a front view of an adjustable support member, consistent with various embodiments.

FIG. 12 illustrates a front view of an adjustable support member 14, consistent with various embodiments. The selected position may include the adjustable support member 14 in a collapsed position or an extended position. The embodiment as shown in FIG. 12 illustrates the adjustable support member 14 in a collapsed position. The collapsed position may be the shortest length of the adjustable support member 14. In the collapsed position, the static member 27 and the telescoping member 29 may be disposed parallel to one another where the vertical position of the static member 27 is similar to the vertical position of the telescoping member 29. The telescoping member locking mechanism 26 may lock the telescoping member 29 at the collapsed position.

While the telescoping system described herein is used in some embodiments, other embodiments use other types of adjustable support members based upon a variety of constructions. For example, adjustable support member 14 may be comprised of a first extender piece, a second extender piece, and a locking piece. The first extender piece and second extender piece are preferably primarily a dense fabric material containing a series of openings which are utilized by the locking piece to lock each extender in a given position. The locking piece contains a lock mechanism and is preferably a rigid material that is capable of securing the first and second extender pieces in place. For example, some embodiments use plastic. In this embodiment, to increase the length of the extender piece by a desired length, the user releases the lock mechanism on the locking piece and: (1) pulls up on the first extender piece the desired length, then re-enables the lock mechanism so that the first extender piece is locked; (2) pulls down on the second extender piece the desired length, then re-enables the lock mechanism so that the second extender piece is now locked; or (3) pulls up on the first extender piece and pulls down on the second extender piece a total distance equal to the desired length, then re-enables the lock mechanism so that the first extender piece and the second extender piece are now locked.

Figure 13:
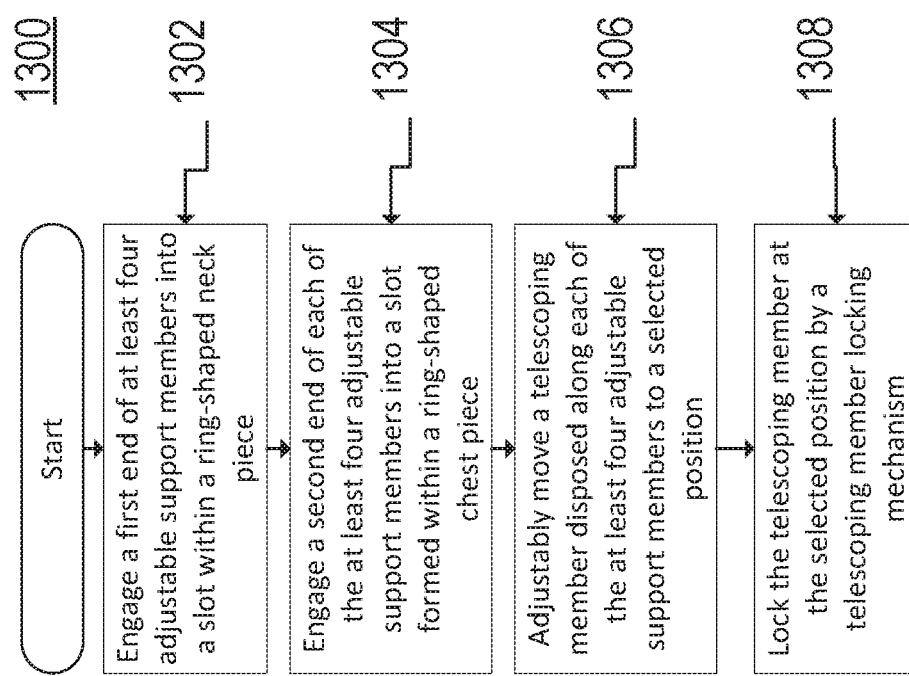
FIG. 13 illustrates a block diagram of a method to engage a neck rehabilitation apparatus, consistent with various embodiments.

FIG. 13 illustrates a block diagram of a method 1300 to engage a neck rehabilitation apparatus, consistent with various embodiments. The method 1300 includes engaging a first end of each of at least four adjustable support members into a slot formed within a ring-shaped neck piece (step 1302). The first end of each adjustable support member may include a slot engaging member that is configured to engage with a slot of the neck piece.

The method 1300 includes engaging a second end of each of the at least four adjustable support members into a slot formed within a ring-shaped chest piece (step 1304). The second end of each adjustable support member may include a slot engaging member that is configured to engage with a slot of the chest piece.

The method 1300 includes adjustably moving a telescoping member disposed along each of the at least four adjustable support members to a selected position (step 1306). The telescoping member may be in parallel with a static member, and the telescoping member is configured to adjustably move along the static member. The selected position may include a position of the telescoping member relative to the static member.

The method 1300 includes locking the telescoping member at a selected position by a telescoping member locking mechanism (step 1308). The method 1300 may include locking the telescoping member by engaging the telescoping member locking mechanism with one of a plurality of slots formed within each telescoping member, wherein the telescoping member locking mechanism extends outwardly from the adjustable support member.

The method 1300 may include engaging a neck wrap to the neck piece and chest piece using buttons disposed on the neck wrap. The neck wrap may include a first piece and a second piece engaged at a periphery of the first piece, where the first piece and second piece form a bladder therein. The method 1300 may include disposing a liquid inside the bladder. The liquid may be warm or cooled to regulate the temperature of the neck wrap.

The method 1300 may include unlocking the telescoping member locking mechanism from the telescoping member. The telescoping member locking mechanism may be unlocked by removing the locking mechanism from an opening formed in the telescoping member.

The method 1300 may include moving the telescoping member to a second position. The second position may differ from the selected position. The telescoping member may repeatedly change positions over the course of rehabilitation to provide varying levels of support to the head and neck of the user. The telescoping member may adjustably move along the static member to the second position. The method 1300 may include locking the telescoping member locking mechanism at the second position.

To equip the device, the length of each adjustable support member may be set to a selected position. Each adjustable support member may include a different selected position. The length of each adjustable support member may be modified by adjustably moving a telescoping member along a static member of the adjustable support member.

Each adjustable support member may be engaged to the neck piece by engaging a first end of each adjustable support member into a slot of the neck piece. Each adjustable support member may include a slot engaging member configured to frictionally engage with a slot. Each adjustable support member may be engaged to the chest piece by engaging a second end of each adjustable support member into a slot of the chest piece. Any order of engaging the neck piece and chest piece to the adjustable support members may be utilized.

The neck piece may be disposed around the lower head and upper neck of the user, and the chest piece may be disposed around the upper chest and lower neck of the user. Each adjustable support member may be disposed along the neck of the user.

In some embodiments, the user may equip the neck rehabilitation apparatus unassisted. However, in some embodiments, the user may be unable to equip the neck rehabilitation apparatus unassisted, and in such embodiments, the user is assisted by a doctor, medical professional, or any other individual capable of adjusting the length of the support members while the user wears the device.

What is claimed is:

1. A neck rehabilitation apparatus, comprising:
   a ring-shaped neck piece comprising a plurality of slots formed through the neck piece;
   a ring-shaped chest piece comprising a plurality of slots formed through the chest piece;
   at least four adjustable support members, each of the at least four adjustable support members comprising:
      a static member, and
      a telescoping member adjustably movable along the static member to a selected position, where the selected position of the telescoping member determines a fixed, spaced relation between the neck piece and the chest piece, the telescoping member comprising:
         a first end engageable with at least one slot formed through the neck piece;
         a second end engageable with at least one slot formed through the chest piece; and
         a telescoping member locking mechanism configured to lock the telescoping member at the selected position; and
   a neck wrap engaged to the neck piece and the chest piece, wherein the neck wrap frictionally engages to the neck piece and chest piece using a plurality of buttons disposed along the neck piece and the chest piece.

2. The neck rehabilitation apparatus of claim 1, wherein each of the at least four adjustable support members include a concave curvature that follows the curvature of a human neck.

3. The neck rehabilitation apparatus of claim 1, further including two front adjustable support members and two rear adjustable support members, where the two rear adjustable support members have a greater length than the two front adjustable support members.

4. The neck rehabilitation apparatus of claim 1, wherein the first end and the second end of each adjustable support member includes a slot engaging member, wherein the slot engaging member at the first end is configured to engage at least one slot of the neck piece, and the slot engaging member at the second end is configured to engage at least one slot of the chest piece.

5. The neck rehabilitation apparatus of claim 1, wherein the telescoping member includes a plurality of openings formed therein.

6. The neck rehabilitation apparatus of claim 5, wherein the telescoping member locking mechanism extends outwardly from the static member, where the telescoping member locking mechanism is configured to frictionally engage with one of the plurality of openings of the telescoping member.

7. The neck rehabilitation apparatus of claim 1, further comprising a chin plate engaged to, and extending upwardly from, the neck piece.

8. The neck rehabilitation apparatus of claim 1, further comprising an over-the-shoulder stabilizer engaged to, and extending downwardly from, the chest piece.

9. An apparatus, comprising:
a ring-shaped neck piece comprising a plurality of slots formed through the neck piece;
a ring-shaped chest piece comprising a plurality of slots formed through the chest piece; and
at least four adjustable support members, each of the at least four adjustable support members comprising:
a static member;
a telescoping member adjustably movable along the static member to a selected position, where the selected position of the telescoping member determines a fixed, spaced relation between the neck piece and the chest piece, the telescoping member comprising:
a first end including a slot engaging member engaged with at least one slot formed through the neck piece;
a second end including a second slot engaging member engaged with at least one slot formed through the chest piece;
a telescoping member locking mechanism locking the telescoping member at the selected position; and
a neck wrap engaged to the neck piece and the chest piece, wherein the neck wrap frictionally engages to the neck piece and chest piece using a plurality of buttons disposed along the neck piece and the chest piece.

10. The apparatus of claim 9, further including a bladder formed within the neck wrap.

11. The apparatus of claim 10, further including a liquid disposed within the bladder.

12. The apparatus of claim 9, further comprising a chin plate engaged to, and extending from, the neck piece, where the chin plate is configured to be disposed below a chin of a user.

13. The apparatus of claim 9, further comprising an over-the-shoulder stabilizer engaged to the chest piece, where the over-the-shoulder stabilizer is engaged to and extends downward from the chest piece.

14. A method to engage a neck rehabilitation apparatus, comprising:
engaging a first end of each of least four adjustable support members into a slot formed through a ring-shaped neck piece;
engaging a second end of each of the at least four adjustable support members into a slot formed through a ring-shaped chest piece;
adjustably moving a telescoping member of each adjustable support member along a static member of each adjustable support member to a selected position;
locking the telescoping member at the selected position by a telescoping member locking mechanism; and
frictionally engaging a neck wrap to the neck piece and the chest piece using a plurality of buttons disposed along the neck piece and chest piece.

15. The method of claim 14, wherein engaging the first end of each of least four adjustable support members includes engaging a slot engaging member with the slot formed through the neck piece, and wherein engaging the second end of each of the at least four adjustable support members includes engaging a second slot engaging member with the slot formed through the chest piece.

16. The method of claim 14, wherein locking the telescoping member includes engaging the telescoping member locking mechanism with one of a plurality of openings formed within the telescoping member, wherein the telescoping member locking mechanism extends outwardly from the adjustable support member.

17. The method of claim 14, further comprising
unlocking the telescoping member locking mechanism from the telescoping member;
moving the telescoping member to a second selected position; and
locking the telescoping member locking mechanism at the second selected position.

* * * * *